United States Patent [19]
DePasquale et al.

[11] Patent Number: 4,618,688
[45] Date of Patent: Oct. 21, 1986

[54] SILANE COMPOSITIONS

[75] Inventors: Ralph J. DePasquale; James M. Evans, both of Jacksonville; Paul W. Kremer, Gainesville, all of Fla.

[73] Assignee: SCM Corporation, New York, N.Y.

[21] Appl. No.: 722,324

[22] Filed: Apr. 12, 1985

[51] Int. Cl.$^4$ .............................. C07F 7/10; C07F 7/18
[52] U.S. Cl. ..................................... 556/419; 556/420; 556/421; 427/387; 427/388.1; 427/409; 106/14.05; 106/14.15; 252/389 R; 548/110
[58] Field of Search ...................... 556/419, 420, 421; 427/387, 388.1, 409; 106/14.15, 14.05; 252/389 R; 548/110

[56] References Cited

U.S. PATENT DOCUMENTS

| | | | |
|---|---|---|---|
| 3,629,309 | 12/1971 | Bailey et al. | 556/419 |
| 4,062,693 | 12/1977 | Berger | 106/308 Q |
| 4,105,465 | 8/1978 | Berger | 106/308 Q |
| 4,151,154 | 4/1979 | Berger | 260/40 R |

Primary Examiner—Paul F. Shaver
Attorney, Agent, or Firm—R. A. Sturges

[57] ABSTRACT

There is provided a novel class of alkoxy silanes useful as corrosion inhibitors for metal surfaces and characterized by an alkylene group attached to silicon through a Si—C linkage. These compounds also contain nitrogen as an amine or an imine group in a linear or cyclic structure. Sulfur and/or a carbonyl or thiocarbonyl group may also be present. The invention also provides a method of inhibiting corrosion of metal surfaces by applying a coating containing or consisting of a novel silane as above described.

22 Claims, No Drawings

SILANE COMPOSITIONS

This invention relates to novel silanes characterized by an alkylene group attached to silicon at one end and functional groups at the other end including amine or amide and carbonyl or thiocarbonyl. These materials have special utility as corrosion inhibitors for metal, particularly iron and steel.

BACKGROUND OF THE INVENTION AND PRIOR ART

The degradative attack of a metal by its environment through chemical or electrochemical means is a description of the corrosive process. The literature deals extensively with agents that retard corrosion of metal surfaces. Using iron as a representative metal, corrosion has been viewed to occur at sites consisting of electromotive cells. The anode region converts iron to iron (II) with electron liberation. To maintain electrical neutrality, the cathode region finds protons (hydronium ions) capturing electrons evolving hydrogen under acid conditions or oxygen reduced to hydroxide in the presence of water under alkaline or neutral conditions. The ferrous hydroxide produced from the coupled electrochemical reaction is subsequently oxidized to ferric oxide, rust, which due to its larger expansion by comparison to iron metal ruptures and fails to form a protective layer on the iron surface.

Agents that interfere with any of the above critical steps in the corrosion cycle act as inhibitors. The present invention relates to novel compounds that contain two structural features acting in concert to control corrosion. The first is an alkoxy silane that can form a passivating multidimensional cohesive film barrier capable of adhesive covalent bonding to the surface of many metals in the presence of moisture. The second is a carbon bound substituent on the silicon center of the alkoxy silane, immobilized in molecular proximity to the metal surface by the above described bonding and designed to act as either a resistive/hydrophobic, pH control, ion immobilizing or free radical inhibiting center. The examples below demonstrate the synthesis of these materials and their corrosive reducing properties when applied to iron surfaces in a prescribed manner.

The use of silanes to inhibit corrosion of iron or steel is not broadly new. Representative examples of prior disclosures include U.S. Pat. No. 3,890,269 to Martin teaches the preparation of aminofunctional organopolysiloxanes which are said to be useful as sizing agents and as corrosion inhibitors. U.S. Pat. No. 3,759,751 discloses a wash primer comprising an epoxy resin, an inorganic chromate, and an aminosilane for use on aircraft surfaces. British Pat. No. 1,409,483 discloses methylaminoethyltriethoxysilane as a corrosion inhibitor for nonferrous metals and alloys. U.S. Pat. No. 4,310,575 to Khayat discloses trimethylsilylacetamide as a corrosion inhibitor for steel. The present invention provides novel silane compounds which have utility as corrosion inhibitors for metal surfaces.

BRIEF STATEMENT OF THE INVENTION

Briefly stated, the present invention is in novel silanes having the general formula:

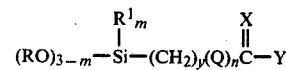

wherein R and $R^1$ are independently selected from alkyl groups containing from 1 to 3 carbon atoms; X is selected from (a) chalcogens, (b) $NCH_2CH_2Y$, where Y is N-saturated or N-unsaturated $C_1$-$C_{20}$ alkyl or cycloalkyl, (c) $N$—$C_6H_4$-ortho-Y where Y is S; Q is $CH_2S$; and, when X is chalcogen, Y is selected from NH-saturated or NH-unsaturated $C_1$-$C_{20}$ alkyl or cycloalkyl, NH—$CH_2CH_2CH_2N(CH_3)_2$, and $NHNH_2$; m is zero to 3, y is 1 to 3, and n is zero to 1.

This invention is also in a method of inhibiting corrosion of a metal substrate by applying to the surface a thin coating (<0.001") of a silane having the above general formula.

The term "aliphatic" shall be deemed to include cycloaliphatic.

DETAILED DESCRIPTION AND SPECIFIC EXAMPLES

The novel compounds of the present invention are broadly lower alkyl, lower alkoxy, or mixed lower alkyl and lower alkoxy silanes characterized by an alkylene group attached to the silicon atom by a Si—C linkage. These compounds also contain nitrogen as an amine or an imine group in a linear or cyclic structure. Sulfur and/or a carbonyl or thiocarbonyl group may also be present.

Typical examples of silane compounds within the above class of novel compounds are as follows: In these examples Me=methyl, Et-ethyl, Pr=propyl or isopropyl, $\phi$=phenyl and $C_6H_{11}$=cyclohexyl.

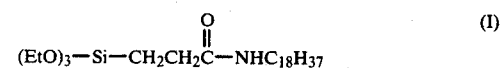

(I)

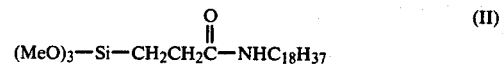

(II)

(III)

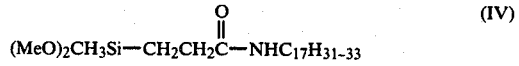

(IV)

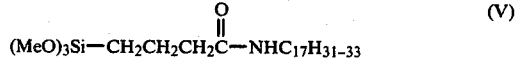

(V)

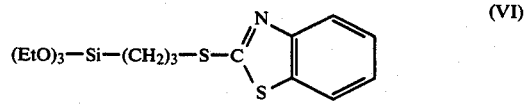

(VI)

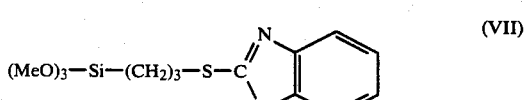

(VII)

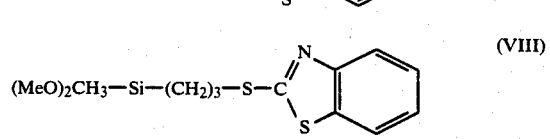

(VIII)

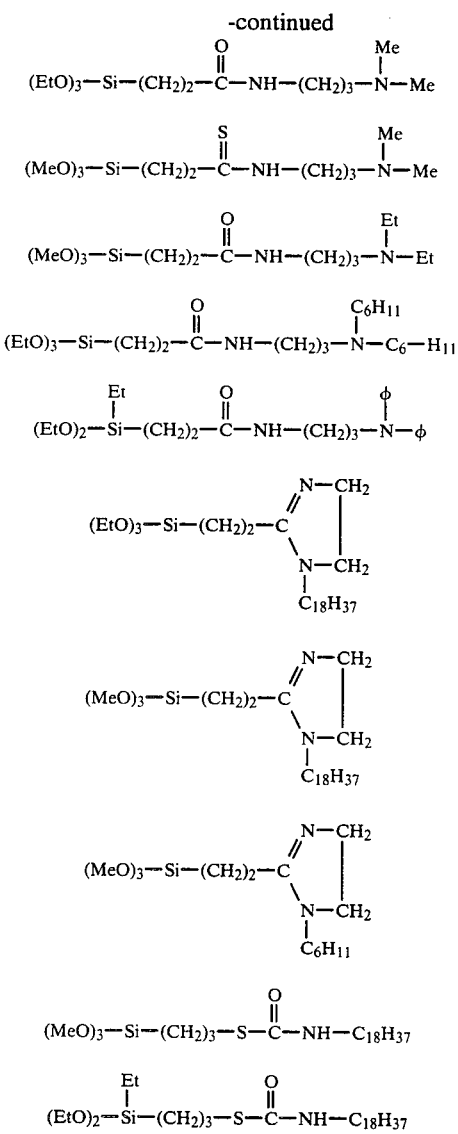

The following examples illustrate procedures by which members of the foregoing typical examples may be prepared. The Roman numerals following the titles in these examples correspond to those given above.

EXAMPLE 1

Preparation of Beta-(Triethoxysilyl)-N-Octadecylpropionamide (I)

A solution of 264 g (1.0 mole) of beta-carbethoxytriethoxysilane, 250 g (0.91 mole) of octadecylamine, and 8.0 ml of 25% NaOMe in methanol was slowly heated under nitrogen to 150° C. with continuous removal of the evolved alcohols. After 18 hr. at 150° C., the reaction was cooled to ambient temperature affording 460 g (98% yield) of white waxy solid m.p. 50°-52° C. IR (neat film) 3400, 2900, 1620, 1540, 1430, 1200, 1190, 1000, 950 cm$^{-1}$. NMR (CDCl$_3$) 0.4–1.0 (m; 5H), 1.0–1.9 (m; 41H), 2.2 (br t; 2H), 3.2 (br t; 2H), 3.82 (q; 6H), 6.0 (br; 1H) ppm.

This example represents the best mode of carrying out our invention.

EXAMPLE 2

Preparation of Beta-(Trimethoxysilyl)-N-Octadecylpropionamide (II)

The trimethoxy analogue of the product of Example I is prepared in the same manner as given in Example I substituting on a mole for mole basis beta-carbethoxytrimethoxy-silane for the beta-carbethoxytriethoxysilane of Example I. In a similar manner (III), (IV) and (V) may be prepared.

EXAMPLE 3

Preparation of 3-(2-Mercaptobenzothiazole)Propyltrimethoxysilane and Analogues (VII)

To a slurry of 267 g (1.6 mole) of 2-mercaptobenzothiazole in 750 ml of dry methanol under nitrogen at 24° C. was added 345 g (1.6 mole) of a 25% solution of NaOMe in methanol, giving a red-orange solution and a slight temperature rise to 37° C. After 20 min of stirring, 306 g (1.54 mole) of 3-chloropropyltrimethoxysilane was added in one portion and the reaction was heated at reflux for 44 hr. After cooling to ambient temperature, the solids (NaCl) were removed by filtration and washed with 100 ml of dry methanol. The combined filtrate and wash solvent were stripped of solvent on a rotary evaporator giving 526 g of a viscous, dark red-brown oil. Distillation of the oil gave 359 g (71%) of product with a boiling point of 170°–172° C. at 0.35 torr. IR (neat) 3050, 1680, 1550, 1455, 1430, 1190, 1080, 995, 810, 755, 725 cm$^{-1}$. NMR (CDCl$_3$) 0.6–1.0 (m; 2H), 1.5–2.1 (m; 2H), 2.5–2.8 (m; 2H), 3.55 (s, 9H), 7.2–7.9 (m; 4H) ppm. The analogues (VI) and (VIII) may be prepared in a similar manner by substituting an equimolar amount of the corresponding silane.

EXAMPLE 4

Preparation of N-(3-Dimethylaminopropyl)Carboxamidoethyltriethoxysilane and Analogues (IX)

A mixture of 264 g (1.0 mole) carboxyethyltriethoxysilane, 112 g (1.1 mole) N,N-dimethyl-1,3-propanediamine, and 5.0 ml of 25% NaOMe in methanol under nitrogen was gradually heated to 150° C. over 3 hours with removal of the evolved methanol/ethanol (40 g). IR analysis of the reaction mixture revealed a small ester peak at 1740 cm$^{-1}$ and a large amide peak at 1650 cm$^{-1}$. The reaction was fractionally distilled at 145°–153° C./0.05 torr giving 255 g (80%) of pale yellow oil. IR (neat) 3300, 1650, 1545, 1170, 1100, 1080, 965, 790 cm$^{-1}$. NMR (CDCl$_3$) 0.9 (m; 2H), 1.2 (t; 9H), 1.7 (m; 2H), 2.20 (s; 6H), 2.3 (m; 4H), 3.2 (m; 2H), 3.8 (q; 6H), 7.2 (br s; 1H) ppm. The analogues (X), (XI), (XII) and (XIII) are prepared in a manner similar in all respects except using equimolar substitution of the appropriate starting material of Example 4 by the corresponding material required by the desired analogue.

EXAMPLE 5

Preparation of 1-Octadecyl-2-(Beta-Triethoxysilylethyl)-4,5-Dihydroimidazole and Analogues (XIV)

A mixture of 70 g (0.27 mole) 2-(beta-triethoxysilylethyl)-4,5-dihydroimidazole and 120 g (0.36 mole) octadecyl bromide was heated at 160° C. under nitrogen for four hours. Cooling to ambient temperature afforded a viscous, brown solution which was stripped of excess octadecyl bromide at 160° C. and 0.1 torr. The resulting hydrobromide salt was a viscous brown oil that solidified on prolonged standing.

A portion of the salt (7.92 g; 13.4 mmol) was dissolved in 50 ml of dry hexane and 2.90 g (13.4 mmol) of 25% NaOMe in methanol was added in one portion, immediately forming a white precipitate (NaBr). After being stirred at ambient temperature for 1 hour, the solution was filtered through a medium glass frit, and the collected precipitate was washed with 10 ml of hexane. The combined filtrates were evaporated at 50° C./20 torr to give 6.26 g (91%) of sl. cloudy brown oil that solidified on standing. IR (neat film) 2920, 2850, 1610, 1460, 1370, 1250, 1115, 900, 720 cm$^{-1}$. NMR (CDCl$_3$) 0.4–1.0 (m; 5H), 1.0–1.6 (m; 41H), 2.0–2.4 (m; 2H), 2.9–3.5 (m; 6H), 3.70 (q; 6H) ppm.

To prepare the imidazole above, a solution of beta-cyanoethyltriethoxysilane (651 g, 3.0 mole) and 1,2-diaminoethane (540 g, 9.0 mole) was saturated with H$_2$S at 25° C., and the reaction was allowed to stand for 96 hours before heating to 60° C. for three hours. Two layers formed; the upper layer was separated and distilled to yield a center cut of 330 g (42% yield) of product (b.p. 110° C. at 0.1 torr). NMR (CDCl$_3$) 0.94 (m; 2H), 1.20 (t; 9H), 2.28 (m; 2H), 3.53 (s; 4H), 3.80 (q; 6H), 6.77 (s; 1H) ppm. IR (neat film) 3140, 2960, 1610, 1500, 1090, 800 cm$^{-1}$.

The analogues (XV) and (XVI) are prepared in a manner similar in all respects, except using equimolar substitution of the appropriate starting material of this Example 5 by the corresponding material required by the desired analogue.

EXAMPLE 6

Preparation of N-Octadecyl-S-(3-Trimethoxysilylpropyl)Thiocarbamate and Analogues (XVII)

To 19.6 g (0.10 mole) of 3-mercaptopropyltrimethoxysilane and 0.2 ml of triethylamine under nitrogen was added 29.5 g (0.10 mole) of octadecylisocyanate over a 15 min period. The reaction was warmed to 80° C. for 5 min and then cooled to ambient temperature, giving a waxy white solid. IR (neat film) 3340, 2910, 2850, 1645, 1505, 1470, 1200, 1070, 815, 725 cm$^{-1}$. NMR (CDCl$_3$) 0.4–1.0 (m; 5H), 1.1–2.0 (m; 34H), 2.90 (t; 2H), 3.0–3.3 (m; 2H), 3.53 (s; 9H), 5.65 (br; 1H) ppm.

The analogues (XVIII), XIX, (XX) and (XXI) are prepared in a manner similar in all respects, except using equimolar substitution of the appropriate starting material of this Example 6 by the corresponding material required by the desired analogue.

Specimen Preparation and Testing Procedure

A 0.5, 1, 2 or 5% (by weight) of the silane corrosion inhibitor (Roman Numeral) solution was prepared in 10% aqueous ethanol. A 2"×4" metal specimen of non-phosphated cold rolled steel (CRS), or phosphated cold rolled steel (Phos-CRS), was dipped into the inhibitor solution, air dried, then oven dried at 90° C. for 30 minutes, and cooled to ambient temperature. The treated specimen was attached to a Princeton 350A corrosion meter cell as the working electrode. The cell uses a standard calomel electrode as reference and two high density graphite rods as counter electrodes. Tap water and in some cases, 5% aqueous NaCl served as test solutions. The above potentiodynamic polarization technique provides data based on current-potential plots from which can be derived corrosion potentials, corrosion currents and corrosion rates of specimens treated with inhibitors, relative to controls. Details for carrying these measurements will be found in the Journal of Coatings Technology, Volume 56, No. 714, July 1984, pages 31–41, in an article by R. G. Groseclose et al.

Electrochemical Technique of Corrosion Tests

According to the procedure described in the article by Groseclose et al, supra., a PAR Model 350A was used to evaluate the corrosion rate of specimens using a technique called "Polarization Resistance" (or "Linear Polarization"). A measurement is performed by scanning through a potential range which is very close to the corrosion potential, $E_{corr}$ (the potential at which the rate of oxidation is exactly equal to the rate of reduction). In these experiments, the range was ±25 mV about $E_{corr}$. The resulting current is plotted versus potential. The slope of the curve at $E_{corr}$ allows a determination of the corrosion current density, $I_{corr}$. The value for $I_{corr}$ was used to calculate the absolute corrosion rate, expressed in milli-inches (0.001 in.) per year (MPY).

While all examples demonstrate an ability to inhibit corrosion of steel, compound (I) provided especially significant corrosion inhibition. Compound (I) has a fatty acid residue in its structure, and accordingly stearic acid and hexadecylamine were tested as controls. They showed no corrosion inhibition. Hexadecylamine in fact gave a high rate of corrosion.

| SUMMARY OF CORROSION RESULTS[a] | | | |
|---|---|---|---|
| | CRS | | Phos-CRS |
| Treatment Solution | Tap Water | 5% NaCl | 5% NaCl |
| Control - 1% aq. EtOH[b] | 5.1 mpy | 16.5 mpy | 5.8 mpy |
| Control - 10% aq. EtOH | 4.5 | 12.0 | 7.2 |
| "Chrome Rinse"[c] | | | 18.6 |
| 0.5% (I)[b] | 3.6 | | |
| 2.0% (I)[b] | 0.11 | 6.3 | 0.058 |
| 5.0% (VI) | 2.6 | | |
| 5.0% (IX) | 4.4 | | |
| 0.5% (XIV)[b] | 4.2 | | |
| 2.0% (XIV)[b] | 1.6 | | |
| 0.5% (XVII)[b] | 3.1 | 23.0 | |
| 2.0% (XVII)[b] | 0.61 | 21.8 | |

[a]Results are in mils-per-year (mpy).
[b]The sample was treated in 1% aq. EtOH at the boil; all others were from 10% aq. EtOH at room temperature.
[c]A commercially prepared sample of cold-rolled steel (CRS) that had been phosphated and chromated.

There has thus been provided a novel class of silanes characterized by an alkylene group attached to the silicon atom by a Si—C linkage. These compounds also contain nitrogen as an amine or an imine group in a linear or cyclic structure. Sulfur and/or a carbonyl or thiocarbonyl group may also be present. These materials are particularly effective anticorrosion agents when applied as a coating to a metal substrate, particularly steel. These inhibitors may be used as primers on clean metal surfaces. Adhesion of top or finish coats will also be improved with these materials as additives.

What is claimed is:

1. A silane having the general formula:

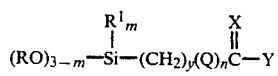

wherein R and R[1] are independently selected from alkyl groups containing from 1 to 3 carbon atoms; X is selected from (a) chalcogens, (b) $NCH_2CH_2Y$, where Y is N-saturated or N-unsaturated $C_1-C_{20}$ alkyl or cycloalkyl, (c) $N-C_6H_4$-ortho-Y where Y is S; Q is $CH_2S$; and, when X is chalcogen, Y is selected from $NH-CH_2CH_2CH_2N(CH_3)_2$, and $NHNH_2$; m is zero to 3, y is 1 to 3, and n is zero to 1.

2. A silane as defined in claim 1 wherein m is O.
3. A silane as defined in claim 1 wherein m is 3.
4. A silane as defined in claim 1 wherein y is 3.
5. A silane as defined in claim 1 wherein n is 0.
6. A silane as defined in claim 1 wherein X is oxygen.
7. A silane as defined in claim 1 wherein X is sulfur.
8. A silane as defined in claim 1 wherein m is 0, y is 3 and n is 0.
9. A silane as defined in claim 1 wherein m is 1, y is 3 and n is 0.
10. A silane as defined in claim 1 wherein m is 0, y is 3, n is 0 and X is oxygen.
11. A silane as defined in claim 1 which is beta-(triethoxysilyl)-N-octadecylpropionamide.
12. A silane as defined in claim 1 which is beta-(trimethoxysilyl)-N-octadecylpropionamide.
13. 3-(2-Mercaptobenzothiazole)propyltriethoxysilane.
14. A silane as defined in claim 1 which is N-(3-Dimethylaminopropyl)carboxamidoethyltriethoxysilane.
15. 1-Octadecyl-2-(beta-triethoxysilylethyl)-4,5-dihydroimidazole.
16. N-Octadecyl-S-(3-trimethoxysilylpropyl)thiocarbamate.
17. The method of improving the resistance of a metal substrate to corrosion which comprises applying to the surface thereof a silane having the general formula:

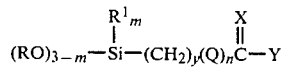

wherein R and R[1] are independently selected from alkyl groups containing from 1 to 3 carbon atoms; X is selected from (a) chalcogens, (b) $NCH_2CH_2Y$, where Y is N-saturated or N-unsaturated $C_1-C_{20}$ alkyl or cycloalkyl, (c) $N-C_6H_4$-ortho-Y where Y is S; Q is $CH_2S$; and, when X is chalcogen, Y is selected from NH-saturated or NH-unsaturated $C_1-C_{20}$ alkyl or cycloalkyl, $NH-CH_2CH_2CH_2N(CH_3)_2$, and $NHNH_2$; m is zero to 3, y is 1 to 3, and n is zero to 1.

18. The method of claim 17 wherein the silane is beta-triethoxysilyl)-N-octadecylpropionamide.
19. A method as defined in claim 17 wherein R is methyl or ethyl, m is O, y is 3, n is O, X is oxygen and Y is NH-saturated or NH-unsaturated $C_1-C_{20}$ alkyl or cycloalkyl.
20. A method as defined in claim 19 wherein Y is N-octadecyl, or N-octadecenyl.
21. A method as defined in claim 17 wherein R is methyl or ethyl, m is 1, y is 3, R[1] is methyl n is O, X is oxygen and Y is NH-saturated or NH-unsaturated $C_1-C_{20}$ alkyl or cycloalkyl.
22. A method as defined in claim 21 wherein Y is N-octadecyl or N-octadecenyl.

* * * * *